US012661529B1

(12) United States Patent
Price

(10) Patent No.: US 12,661,529 B1
(45) Date of Patent: Jun. 23, 2026

(54) X-RAY FLASH RADIOTHERAPY DEVICES AND METHODS

(71) Applicant: James Russell Price, Delray Beach, FL (US)

(72) Inventor: James Russell Price, Delray Beach, FL (US)

( * ) Notice: Subject to any disclaimer, the term of this patent is extended or adjusted under 35 U.S.C. 154(b) by 0 days.

(21) Appl. No.: 19/066,716

(22) Filed: Feb. 28, 2025

(51) Int. Cl.
| | |
|---|---|
| *A61N 5/10* | (2006.01) |
| *H01J 35/12* | (2006.01) |
| *H01J 35/14* | (2006.01) |

(52) U.S. Cl.
CPC ............ *A61N 5/1078* (2013.01); *H01J 35/12* (2013.01); *H01J 35/14* (2013.01); *A61N 2005/1089* (2013.01)

(58) Field of Classification Search
None
See application file for complete search history.

(56) References Cited

U.S. PATENT DOCUMENTS

| | | | |
|---|---|---|---|
| 5,442,678 A | 8/1995 | Dinsmore et al. | |
| 10,607,802 B2 | 3/2020 | Fishman et al. | |
| 11,045,667 B2 | 6/2021 | Fishman | |
| 11,173,325 B2 | 11/2021 | Parry et al. | |
| 11,521,820 B2 | 12/2022 | Fishman et al. | |
| 2005/0111624 A1* | 5/2005 | Yada ..................... | H01J 35/065 |
| | | | 378/136 |
| 2012/0314837 A1* | 12/2012 | Tsujii ..................... | H01J 35/18 |
| | | | 378/143 |

| | | | |
|---|---|---|---|
| 2013/0259207 A1* | 10/2013 | Omote .................... | H01J 35/13 |
| | | | 378/143 |
| 2015/0063546 A1* | 3/2015 | Caiafa ..................... | H05G 1/50 |
| | | | 378/113 |
| 2018/0289977 A1 | 10/2018 | Fishman | |
| 2022/0305292 A1 | 9/2022 | Harper et al. | |
| 2022/0387824 A1 | 12/2022 | Bourhis et al. | |
| 2023/0241413 A1 | 8/2023 | Behbahani et al. | |
| 2024/0090112 A1 | 3/2024 | Agustsson et al. | |

(Continued)

FOREIGN PATENT DOCUMENTS

| | | |
|---|---|---|
| WO | 2021113323 A1 | 6/2021 |
| WO | 2023002348 A1 | 1/2023 |

OTHER PUBLICATIONS

McGregor, Minni, Herold, Superficial Radiation Therapy for the Treatment of Nonmelanoma Skin Cancers, J Clin Aesthet Dermatol. Dec. 2015;8(12):12-14.

(Continued)

*Primary Examiner* — Hoon K Song
(74) *Attorney, Agent, or Firm* — Allen F. Bennett; Bennett Intellectual Property

(57) ABSTRACT

An x-ray FLASH radiotherapy device uses an electron beam to generate x-rays on a target element. The focal area on the target element is about 1 to about 12 cm². The target element is separated from a radiotherapy patient by a thin aerogel insulator. Using about 50 to 200 kV of power, the x-ray FLASH radiotherapy device administers 40 Gy/s of radiation or more during short bursts or pulses of one second or less. Due to the short duration of these pulses, heating of the target element is limited, thereby reducing the source to surface distance between the radiation source and the patient.

6 Claims, 2 Drawing Sheets

(56)                    References Cited

U.S. PATENT DOCUMENTS

2025/0164662 A1*    5/2025    Harms    .................... G01V 5/12

OTHER PUBLICATIONS

Yufan, Hyunsoo, Breitkreutz, Mascia, Moeckli, Bourhis, Schuler, Maxim, Loo, Technological Basis for Clinical Trials in FLASH Radiation Therapy: A Review, Applied Radiation Oncology, Jun. 2021.

Gao, Liu, Chang, Charyyev, Zhou, Bradley, Liu, Yang, "A Potential Revolution in Cancer Treatment: A Topical Review of FLASH Radiotherapy" J Appl Clin Med Phys. 2022.23;e113790.

* cited by examiner

X-RAY FLASH RADIOTHERAPY DEVICES AND METHODS

CROSS-REFERENCE TO RELATED APPLICATIONS

This application claims priority to U.S. Provisional Application Ser. No. 63/559,439 filed on Feb. 29, 2024, the contents of which are hereby incorporated in their entirety.

STATEMENT REGARDING FEDERALLY SPONSORED RESEARCH OR DEVELOPMENT

Not Applicable.

NAMES OF PARTIES TO A JOINT RESEARCH AGREEMENT

Not Applicable

REFERENCE TO SEQUENCE LISTING, A TABLE, OR A COMPUTER PROGRAM LISTING APPENDIX SUBMITTED ON A COMPACT DISC AND INCORPORATION-BY-REFERENCE OF THE MATERIAL

Not Applicable.

COPYRIGHT NOTICE

Not Applicable

BACKGROUND OF THE INVENTION

Field of the Invention

The present invention relates to devices and methods for cancer radiotherapy. More particularly, the invention relates to devices for administering FLASH x-ray radiotherapy at a low source to surface distance.

Description of the Related Art

Cancer is a dominant worldwide cause of death. Skin cancer, a term collectively comprising melanoma and non-melanoma skin cancers (such as basal cell carcinoma [BCC] and squamous cell carcinoma [SCC]), is the most common form of cancer in the United States, with an estimated 9,500 cases diagnosed each day. Between 1994 and 2014, the diagnosis and treatment of nonmelanoma skin cancer increased by 77%; for BCC and SCC, 3.6 million and 1.6 million cases, respectively, are diagnosed each year in the US. According to the American Academy for Dermatology, around 4.9 million U.S. adults were treated for skin cancer each year from 2007 to 2011, for an average annual treatment cost of $8.1 billion. The skin cancer treatment market is projected to grow with a CAGR of 7.3% through 2031. Around 2010, treatment of nonmelanoma skin cancer started growing exponentially. This is due to the approval of reimbursement codes and targeting of dermatologists for treatment devices.

The most common treatment for BCC is surgical removal, which is effective but cosmetically undesirable, or radiation therapy (RT), which is also effective without causing cutting, bleeding or scarring, but can damage non-malignant tissues and often requires up to 20 visits (fractions) per patient. For more aggressive/advanced tumors or those than cannot be treated effectively with surgery or radiation, chemotherapy agents such as vismodegib, sonidegib, 5-FU, and cisplatin are used, which can be effective only for topical BCCs and are expensive. The most common treatment for SCC is surgical removal, which is curative in 98-99% of cases but has the same poor cosmetic outcomes as in BCC. Thus, development of effective and safe treatment technology that yields successful survival outcomes while improving quality of life both during and after treatment would improve the lives of patients immeasurably.

Since the pioneered work of Roentgen and Marie Curie in the early 20th century, radiotherapy remains an essential tool for treating cancer. Conventional radiotherapy treatment generally aims at administering a total dose of 20 to 70 Grays ("Gy") to each tumor, typically in doses of 2 Gy per fraction, each fraction being administered over several seconds to minutes. Recent developments in radiotherapy allowed these treatments to be more precise and more effective, but remaining side effects, particularly damage to healthy tissues, are still a problem. Delivering high curative radiation doses to tumors depends on the ability to spare normal tissues from harmful effects of radiation. Over the last century, both fractionation and precise volume optimization appeared as the most powerful tools to obtain a differential effect between normal tissues and tumors thereby minimizing the side effects.

FLASH radiotherapy is an emerging radiotherapy regime that appears to reduce radiation-induced toxicities while maintaining a tumor response similar to that of more conventional radiotherapy regimes. FLASH radiotherapy may be characterized as delivering a high radiation rate, e.g., greater than about 40 Gy per second, that allows for a total therapeutic dose, or large fractions of a total radiation dose, to be delivered in parts of a second, compared to several seconds to minutes for conventional radiotherapy. For example, a conventional radiotherapy treatment may include a total dose of 12-25 Gy delivered at a rate of up to 0.4 Gy/s, requiring minutes of treatment time. In contrast, FLASH radiotherapy may deliver a similar total therapeutic dose at a rate of 40 Gy/s or higher, requiring a fraction of a second of treatment time. Up to half of the non-melanoma skin cancers treated in the United States could potentially be treated with FLASH radiotherapy using fewer treatments, or a single treatment.

Many current efforts focus on utilizing proton therapy (particle) and linear accelerators (electrons) for FLASH therapy. Electron therapy is very effective but utilizes large linear accelerators (linacs), which is costly and ties up equipment that is also used for deeper seated tumors. Proton therapy is very precise, but also would utilize particle accelerators that are designed for other tumors; both of these solutions are very expensive.

Brachytherapy utilizes a source that is in contact with or very close to the skin. It is relatively inexpensive to generate x-rays for radiotherapy. However, only a few studies have investigated X-ray (photons) FLASH radiotherapy or brachytherapy. Current superficial x-ray sources use an x-ray tube with an internal target, a small focal spot to emit x-rays. One hindrance to effective FLASH radiotherapy is that x-ray generating devices typically produce very high levels of heat. This requires an x-ray source to be separated from a patient's body by enough space or insulation to prevent burning the patient. Typically, x-ray sources are contained within a vacuum chamber and/or are positioned tens of centimeters away. Because x-rays follow the "1 over $r^2$ rule", i.e. they dissipate rapidly with distance. X-ray sources generate substantial heat, and to move an x-ray source close enough to achieve a 40 Gy/s therapeutic dosage, requires moving the x-ray source so close that the emitted heat burns the area being treated.

One method to compensate for the loss of intensity as distance increases is to utilize two or more separate x-ray sources all focused on a single location of a patient. However, utilizing several x-ray sources simultaneously not only multiplies the amount of equipment, and therefore cost, of such a device and procedure, it also requires substantially more precision to accurately guide a plurality of x-ray beams to a single source.

The above-described deficiencies of today's systems are merely intended to provide an overview of some of the problems of conventional systems, and are not intended to be exhaustive. Other problems with the state of the art and corresponding benefits of some of the various non-limiting embodiments may become further apparent upon review of the following detailed description.

In view of the foregoing, it is desirable to provide a relatively simple, lower cost radiation device for treating skin cancers. It is also desirable to provide an X-ray based FLASH radiotherapy treatments capable of delivering a therapeutic dose of radiation (e.g. >40 Gy/sec) using uniformly distributed x-rays to malignant tissue in less than one second, sparing healthy tissues, at a rate capable of safely treating skin cancer in a single delivery that will save treatment time, cosmesis, and money while providing a superior treatment for nonmelanoma skin cancer.

BRIEF SUMMARY OF THE INVENTION

Disclosed is a device and use thereof for a FLASH radiotherapy device for treating skin cancers. The device of the present invention includes an electron beam generator, a drift tube, a target element and a thin insulator. It may optionally include a vacuum manifold. The generator creates an electron beam which travels down the drift tube and impinges upon the target element, causing the target to emit x-rays. The devices and methods of use thereof utilize a "spread out focal spot" to create a larger source that can provide higher dose rates for FLASH radiotherapy. The electron beam may be focused and steered to create a "flat" beam profile, evenly distributed over the focal spot. The radiation dose may be adjusted by manipulating the energy, beam current and dose rate. The focal spot may be between 1 cm and 5 cm.

In one embodiment, a FLASH radiation therapy device consists of an electron beam generator, a power supply providing 100 to 200 kV to the electron beam generator, and an x-ray target element. A drift tube extends between the electron beam generator and the x-ray target element. A vacuum manifold is placed in line between the electron beam generator and the drift tube, and an insulator covers a distal end of the target element. The device is operated by rapidly activating and deactivating the electron beam generator in order to induce FLASH x-ray radiation from the target element. The vacuum manifold may be removably attached to a distal end of the electron beam generator and removably attached to a proximal end of the drift tube. The x-ray target element may include a disk of diamond substrate having a tungsten coating layer on a proximal end. The insulator is optionally comprised of an insulating disk, i.e. aerogel between 1 and 5 mm thick affixed to a distal end of the target element.

In another embodiment, an X-ray FLASH radiotherapy device includes an electron beam generator, a power supply providing 50 to 200 kV to the electron beam generator, an x-ray target element having a cross-sectional surface area of between 1 and 4 cm, a drift tube extending between the electron beam generator and the x-ray target element, and an insulator covering a distal end of the target element. The electron beam generator may also have a filament in an ionization chamber, a proximal electrode and a switch for rapidly alternating the polarity of the proximal electrode. The switch may be an H bridge. The insulator may comprise a disk of an aerogel having a thickness between 1 and 5 mm. The x-ray target element may have a diamond substrate with a tungsten coating. The power supply may provide the electron beam generator with a voltage between 70 and 100 kV. Two or more focusing magnets may be positioned about the proximal end of the drift tube, and may be slidingly mounted on tracks that allow the one or more focusing magnets to translate between proximal and distal locations along the drift tube. The electron beam generator may have a distal electrode having a polarity opposite to the proximal electrode, wherein the switch for alternating the polarity of the proximal electrode simultaneously alternates the polarity of the distal electrode. The device may also include an annular heat sink extending around the target element. The wherein width of the insulator is substantially equal to the width of the annular heat sink.

In another embodiment, superficial X-ray FLASH radiotherapy is applied to a patient using an X-ray FLASH radiotherapy device comprising an electron beam generator, a power supply providing 50 to 200 Kv to the electron beam generator, an x-ray target element having a cross-sectional surface area of between 1 and 4 cm, a drift tube extending between the electron beam generator and the x-ray target element, and an insulator covering a distal end of the target element. The device is placed between 0.5 and 2 cm from an area of the patient's skin to be treated. The device then emits one or more pulses of X-ray radiation, wherein each pulse is between the 0.1 and 0.5 seconds and a dosage per pulse is greater than 40 Gray/second.

It is therefore an object of the present invention to provide a compact, low power apparatus for and method of treating skin cancer using radiotherapy. It is also an object of the invention to provide medical device technology that delivers FLASH RT, which delivers a therapeutic dose of radiation (>40 Gy/sec) to malignant tissue in <1 second, sparing healthy tissue while delivering a lethal dose of radiation to the malignant tissue, providing superior outcomes with one visit at a lower cost to both the patient and facility. It is also an object of the invention to provide an X-ray based device capable of delivering uniformly distributed x-rays at a rate capable of safely treating skin cancer in a single delivery that reduces treatment time, cosmesis, and money while providing a superior treatment for nonmelanoma skin cancer.

These and other objects and advantages of the present invention will become apparent from a reading of the attached specification and appended claims. There has thus been outlined, rather broadly, the more important features of the invention in order that the detailed description thereof that follows may be better understood, and in order that the present contribution to the art may be better appreciated. There are features of the invention that will be described hereinafter and which will form the subject matter of the claims appended hereto.

BRIEF DESCRIPTION OF THE DRAWINGS

A more complete understanding of the present invention, and the attendant advantages and features thereof, will be more readily understood by reference to the following

Figure 1:
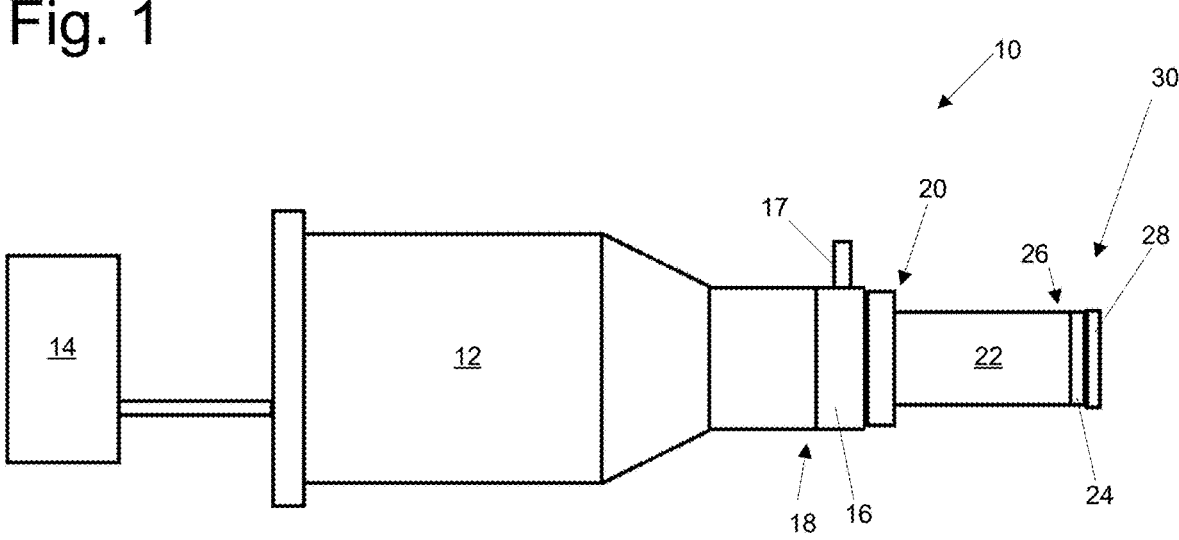
Figure 2:
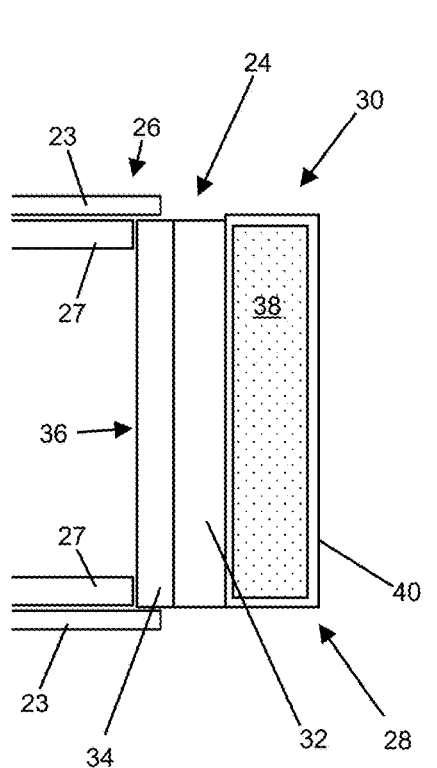
Figure 3:
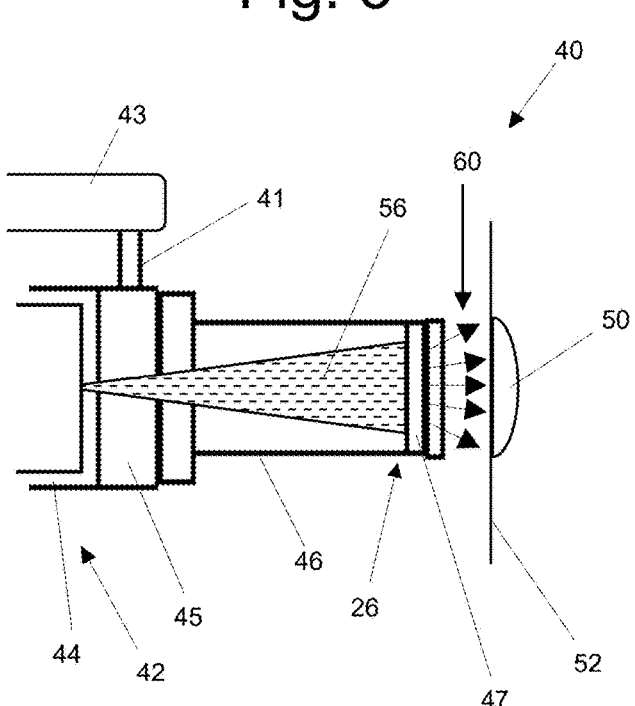
Figures 4, 5:
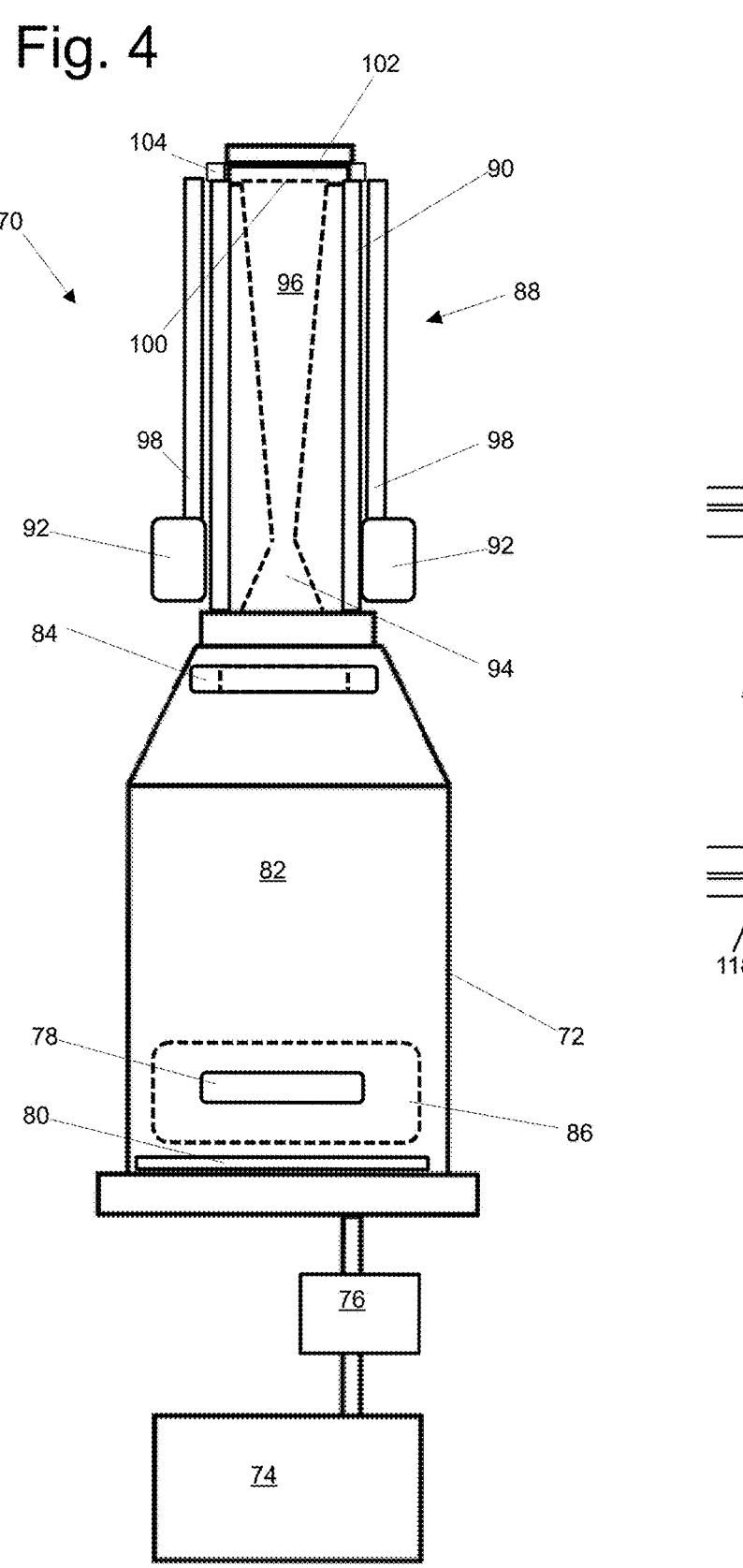

5 detailed description when considered in conjunction with the accompanying drawings wherein:

FIG. 1 is a side elevation view of an x-ray FLASH radiotherapy device in accordance with the principles of the invention;

FIG. 2 is an enlarged cross-sectional view of a distal end of an x-ray FLASH radiotherapy device in accordance with the principles of the invention;

FIG. 3 is a side cross-sectional view of an x-ray FLASH radiotherapy device in use to treat a superficial lesion in accordance with the principles of the invention;

FIG. 4 is a side elevation view of an alternative embodiment of an x-ray FLASH radiotherapy device in accordance with the principles of the invention;

FIG. 5 is a side cross-sectional view of an alternative embodiment of an x-ray FLASH radiotherapy device in use to treat a superficial lesion in accordance with the principles of the invention.

DETAILED DESCRIPTION

The invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The disclosed subject matter is described with reference to the drawings, wherein like reference numerals are used to refer to like elements throughout. In the following description, for purposes of explanation, numerous specific details are set forth in order to provide a thorough understanding of the various embodiments of the subject disclosure. It may be evident, however, that the disclosed subject matter may be practiced without these specific details. In other instances, well-known structures and devices are shown in block diagram form in order to facilitate describing the various embodiments herein. Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

Unless otherwise indicated, all numbers expressing quantities of ingredients, dimensions, reaction conditions and so forth used in the specification and claims are to be understood as being modified in all instances by the term "about". The term "a" or "an" as used herein means "at least one" unless specified otherwise. In this specification and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

For ease of understanding, the following definitions will apply throughout this description. However, no definition should be regarded as superseding any art accepted understanding of the listed terms.

Various embodiments of the disclosure could also include permutations of the various elements recited in the claims as if each dependent claim was a multiple dependent claim incorporating the limitations of each of the preceding dependent claims as well as the independent claims. That is, the combinations of the various components of the invention are not limited to those combinations expressly shown in the Figures. Unless expressly stated otherwise, components described in one embodiment may be interchanged with components of the same name found in other embodiments. Such permutations are expressly within the scope of this disclosure.

Disclosed is are devices and methods of using x-ray FLASH radiotherapy for treating skin cancers. The device of the present invention includes an electron beam generator, a drift tube, a target element, and an insulator. As is known in the art, the device may include a vacuum manifold to maintain a vacuum in the electron beam generator and drift tube. The generator creates an electron beam which travels down the drift tube and impinges upon the transmitting target element, causing the target to emit x-rays. The drift tube may be of a material that shields the external environment from reflected x-rays, or may have a radiation shielding jacket. Rather than attempting to form a highly concentrated x-ray beam within an x-ray tube by impinging an electron beam onto an anode, the present invention uses a relatively large target element and an electron beam that spreads out evenly to cover a large focal spot on the target element. The use of a large focal spot to create a relatively wide beam of x-rays, allows the invention to deliver more than 40 Gy/s over a fraction of a second, i.e. FLASH radiation. The invention obviates the need to collimate the x-rays by placing the target element very close to the area to be treated. Because the radiation time is short, and the electron beam is spread over a relatively large target, the amount of heat generated at the target is minimized. This allows the heat at the target element to dissipate rapidly enough that a relatively small insulator is adequate to prevent burning the patient.

FIG. 1 shows an x-ray FLASH radiation therapy device 10 in accordance with principles of the invention. A power supply 14 provides from about 50 to about 250 kV from to an electron beam generator 12. Those skilled in the art will appreciate that there are a wide variety of electron beam generators suitable for use in generating x-rays. A vacuum manifold 16 may be incorporated into the device 10 between a distal end 18 of the electron beam generator 12 and the proximal end 20 of a drift tube 22. The manifold 16 evacuates the drift tube 22 and/or the electron gun 12. The manifold 16 includes one or more ports 17 for attachments to a means for regulating pressure inside the manifold. In this embodiment, the drift tube 22 is cylindrical and approximately 30 cm in length and about 1 to 3 cm wide.

Referring to FIG. 2, the drift tube 22 may also be surrounded by shielding 23 to prevent any x-rays reflecting off the target from traveling through the outer wall 27 of the drift tube 22. A target element 24 is affixed to the distal end 26 of the drift tube 22. In this embodiment, the shielding 23 extends partially over the target element 24 to shield x-rays emanating transverse to the direction of the electron beam. An insulator 28 is affixed to the target element 24 at the distal end 30 of the FLASH radiation therapy device 10 and is sized to sufficiently cover the distal end of the target element. In this embodiment, the drift tube 22 is cylindrical and both the target element 24 and the insulator 28 are disc-shaped, and both are about 2.5 cm in diameter. Optionally, the target element can be from about 1 to about 5 cm diameter. The shielding 23 of the drift tube 22 may optionally extend partially or completely over the periphery of the target element 24, and may optionally extend partially or completely over the insulator 28. It may be preferable for the target to abut against the shielding or other metallic components in order to dissipate heat more rapidly, as explained below.

The target element 24 of this embodiment at the distal end 26 of the drift tube 22 includes a diamond substrate 32 and a tungsten coating 34 on its proximal end 36. Optionally, the substrate may be formed from other materials such as beryllium, sapphire, alumina, boron nitride or other materials that are substantially transparent to x-rays and are also preferably highly heat conductive. Those skilled in the art will appreciate that substrate materials which are transmissive of x-rays are generally preferred. The insulator 28 in this embodiment comprises a thin aerogel wafer 38 having a thickness 40 between 0.5 and 5 mm, or optionally between 0.7 and 1.5 mm, or optionally of about 1 mm, and is optionally contained in a heat resistant housing 40. The insulator 28 is optionally interchangeable with additional insulators having different thicknesses. In general, it is desirable that the insulator 28 have a thickness of 2 mm or less, but it may optionally be 5 mm or more. Optionally, the aerogel may be replaced with other insulators so long as they are substantially transparent to x-ray radiation and sufficiently insulate the heat of the target element from the patient. The target element may optionally be positively charged.

In use, as shown in FIG. 3, the x-ray FLASH radiation device 40 applies x-ray radiation to a tumor 50 on a patient's skin 52. The port 41 of the manifold 45 is attached to a vacuum source 43. When the vacuum source is actuated, both the manifold 45 and the drift tube 22 are evacuated and maintained at a vacuum pressure to minimize attenuation of the electron beam 56 emitted by the electron beam generator 42. In general, a vacuum pressure of at least $10^{-5}$ torr, for example about $10^{-9}$ torr to $10^{-7}$ torr, is suitable. The electron beam 56 spreads out as it travels out of the aperture of a Wehnelt cap 44 and down the drift tube 46 and impinges upon the a large portion of target element 47. X-rays 60 are then emitted through the substrate 32 and insulator 28 and onto the tumor. Because the target element 24 is close to the tumor 50, 1 cm or less, it is capable of providing a substantial dose of radiation, over 40 Gy/s, under very modest power, e.g. 200 kV or less.

Because the present invention is intended to be applied directly to a tumor on a patient's skin, with the x-ray generating target element placed relatively close to the tumor, precise collimating and directing of the electron beam is unnecessary; the electron beams needs only to be relatively evenly distributed over its large, spread out focal spot. Due to the "differential effect" healthy tissue is not damaged during a very short (less than 1 second) irradiation at very high rates, e.g. greater than 40 Gy/s. This eliminates the necessity for precise focusing and steering of the beam. This allows FLASH radiotherapy to be performed quickly using a simple device requiring relatively little power. Because the radiation is administered over very short time periods, the target element does not reach extreme temperatures and is able to cool substantially in between pulses. This allows the source to surface distance to be reduced to less than 1 cm. The relatively thin insulator is sufficient to protect a patient from the heat generated, which is very modest compared to the heat generated during standard radiotherapy procedures. Those skilled in the art will appreciate that the apparatus and methods disclosed herein are most easily applied to skin cancers. However, the device may also be used in inter-operative radiotherapy techniques.

FIG. 4 shows an alternative embodiment of an x-ray Flash radiotherapy device 70 in accordance with the principles of the invention. In this embodiment, the power supplied to the electron beam generator 72 from the power supply 74 is managed by a controller 76. The electron beam generator 72 includes a heating filament 78 and a proximal electrode 80 in the ionization chamber 82. The beam generator 72 may optionally include a distal electrode 84, which in this embodiment is toroidal. Those skilled in the art will appreciate that the distal electrode 84 can also be a screen or grid. It is relatively common for an electron beam to be actuated by alternating the polarity of the distal electrode 84. However, those skilled in the art will appreciate that beams generated in this fashion are of variable intensity. In this embodiment, the distal electrode 84 is either not activated or charged at all. Optionally, the distal electrode 84 is absent from the device altogether. Instead, the beam pulse is actuated by inverting the polarity of the proximal electrode 80.

The controller 76 includes an H bridge for rapidly alternating the polarity of the proximal electrode 80. When the filament 78 is heated, an electron cloud 86 forms within the ionization chamber 82. The proximal electrode 80 is positively charged, and thus retains the electron cloud 86 and the proximal end of the ionization chamber 82. To generate an electron beam pulse, the H bridge rapidly switches the polarity of the proximal electrode 80 from positive to negative, and then back again to positive. Those skilled in the art will appreciate that the electron beam pulse generated in this manner is of consistent intensity, and the duration of the pulse can be precisely regulated. The electron pulse generated may therefore be carefully regulated by adjusting the power supplied to the filament 78, the charge of the proximal electrode 80, and the duration of the pulse. This, in turn, allows an operator to precisely regulate the intensity, i.e. Gy/s, and duration of the x-ray FLASH radiation. The duration is typically between about 0.1 and about 1 second, and may be about 0.7 seconds.

When a beam pulse is generated, it travels down the drift tube 88, which is surrounded by a shielding jacket 90. Focusing magnets 92 focus the outgoing beam pulse 94 into a concentrated, focused beam pulse 96 near the center of the drift tube 88. This focused beam pulse 96 naturally, and substantially uniformly, expands as it travels down the drift tube 88 due to the natural mutual repulsion of the electrons in the beam. The focusing magnets 92 of this embodiment are slidingly engaged with rails 98, which allows the magnets to translate along the length of the drift tube 88. This allows an operator to adjust the size of the region 100 of the target element 102 struck by the beam pulse 96. Typically, the region 100 struck by the electron beam pulse 96 is between 1 and 4 cm², and is generally more preferably between 2 and 3.5 cm². However, the region 100 can be larger, up to 9 cm².

The x-ray FLASH radiotherapy device 70 also includes an annular heat sink 104 around the target element 102. The heat sink 104 accelerates the dissipation of the heat generated when the beam pulse 96 impinges the target element 102. In FIG. 2, the shielding 23 also absorbs and dissipates some of the heat from the target element. However, many materials that are effective at shielding radiation are not effective heat conductors, and vice versa. Therefore, it may be desirable to include a heat sink 104 formed of a good heat conducting material, such as for example copper or aluminum, while the shielding 98 is formed from a good shielding material, such as for example lead.

FIG. 5 shows an alternative embodiment of an annular heat sink 110 and insulator 112. A target 114 is positioned at a distal end of a drift tube 116 insulated by a shield 118. The target 114 includes a substrate 116 formed of diamonds, beryllium or other material substantially transparent to x-rays. A tungsten film 120 coats the proximal side of the substrate 116. The annular heat sink 110 extends around and abuts the substrate 114. It is also in contact with shield 118. The heatsink 110 of this embodiment also includes an annular fin 122. Optionally, the annular heat sink could include a plurality of radial fins rather than a single annular fin, or combinations thereof. The insulator 112 has a width greater than the width of the target elements 114 and approximately equal to the total width of the heatsink 110. Inclusion of an optional heatsink, as shown in FIGS. 4 and 5, assisted dissipating the heat generated by the electron beam pulse.

Whereas, the present invention has been described in relation to the drawings attached hereto, other and further modifications, apart from those shown or suggested herein, may be made within the spirit and scope of this invention. Those skilled in the art will appreciate that the conception, upon which this disclosure is based, may readily be utilized as a basis for the designing of other structures, methods and systems for carrying out the several purposes of the present invention. Descriptions of the embodiments shown in the drawings should not be construed as limiting or defining the ordinary and plain meanings of the terms of the claims unless such is explicitly indicated. The claims should be regarded as including such equivalent constructions insofar as they do not depart from the spirit and scope of the present invention.

The invention claimed is:

1. A method of applying superficial x-ray FLASH radiotherapy to a patient comprising:

Providing an x-ray FLASH radiotherapy device comprising an electron beam generator, a power supply providing 50 to 200 kV to the electron beam generator, an x-ray target element having a diameter between 1 cm and 5 cm, a drift tube extending between the electron beam generator and the x-ray target element, and an insulator covering a distal end of the target element;

placing the distal end of the device between 0.5 mm and 2 cm from an area of the patient's skin to be treated; and, emitting one or more pulses of x-ray radiation, wherein each pulse is between the 0.1 to and 1 second and a dosage per pulse is greater than 40 Gray/second;

wherein the pulse of x-ray radiation is emitted by the electron gun emitting an electron pulse that impinges on the target element over a focal area having a diameter between 1 cm and 5 cm.

2. The method of applying superficial x-ray FLASH radiotherapy to a patient of claim 1, wherein the electron beam generator comprises a filament in an ionization chamber, a proximal electrode and a switch for rapidly alternating the polarity of the proximal electrode.

3. The method of applying superficial x-ray FLASH radiotherapy to a patient of claim 2, wherein the switch for rapidly alternating a polarity of the proximal electrode comprises an H bridge.

4. The method of applying superficial x-ray FLASH radiotherapy to a patient of claim 3 wherein the radiotherapy device further comprises an annular heat sink extending around the target element.

5. The method of applying superficial x-ray FLASH radiotherapy to a patient of claim 4 wherein the insulator has a width substantially equal to a width of the annular heat sink.

6. The x-ray FLASH radiotherapy device of claim 5 wherein the electron gun has no control anode on a side of the filament opposite to the proximal electrode.

\* \* \* \* \*